United States Patent [19]

Reynolds

[11] Patent Number: 5,015,628

[45] Date of Patent: May 14, 1991

[54] ANTICARIOGENIC PHOSPHOPEPTIDES

[75] Inventor: Eric C. Reynolds, North Balwyn, Australia

[73] Assignees: The University of Melbourne; Victorian Dairy Industry Authority, both of Victoria, Australia

[21] Appl. No.: 563,798

[22] Filed: Aug. 3, 1990

[51] Int. Cl.$^5$ ............... C07K 7/08; A61K 39/12; A61K 39/42; G01N 33/53
[52] U.S. Cl. ............... 514/12; 514/13; 514/15; 514/17; 514/18; 424/49; 530/324; 530/325; 530/326; 530/327; 530/330; 530/352; 530/360
[58] Field of Search ............ 530/324, 325, 326, 327, 530/328, 329, 330, 352, 360; 424/49; 514/18, 17, 15, 13, 12, 21

[56] References Cited

U.S. PATENT DOCUMENTS 4,361,587 11/1982 Brule et al. ............ 435/272

FOREIGN PATENT DOCUMENTS 825115 12/1959 United Kingdom ............ 424/54

OTHER PUBLICATIONS

Huxley, "Cariogenicity in Rats of a Diet Containing Lactalbumin or Casein as the Protein Source", *J Dent Res*, 56(8): 900, Aug. 1977.
Alewood et al., *Proc. of the Amer. Peptide Soc.*, Symp. Peptides, Synthesis, Structure and Function, Rockford, IL, pp. 65–67 (1981).

*Primary Examiner*—Nathan M. Nutter
*Attorney, Agent, or Firm*—Scully, Scott, Murphy & Presser

[57] ABSTRACT

A phosphopeptide or a salt thereof the phosphopeptide having from 5 to 30 amino acids including the sequence

A-B-C-D-E where A, B, C, D and E are independently phosphoserine, phosphothreonine, phosphotyrosine, phosphohistidine, glutamate and aspartate and compositions particularly compositions to teeth including same.

26 Claims, 1 Drawing Sheet

ANTICARIOGENIC PHOSPHOPEPTIDES

This application is a continuation of application Ser. No. 191,162, filed Apr. 12, 1988, now abandoned.

This invention relates to phosphopeptides and compositions containing same.

This invention also relates to caries and gingivitis inhibition.

The present invention provides a phosphopeptide or a salt thereof, the phosphopeptide having from 5 to 30 amino acids including the sequence

A-B-C-D-E where A, B, C, D and E are independently phosphoserine, phosphothreonine, phosphotyrosine, phosphohistidine, glutamate and aspartate.

Preferred phosphopeptides are those wherein A, B and C are independently phosphoserine, phosphothreonine, phosphotyrosine and phosphohistidine and D and E are independently phosphoserine, phosphothreonine, glutamate and aspartate.

Particularly preferred phosphopeptides are those where A, B and C are phosphoserine and D and E are glutamate.

The phospeptide is preferably in substantially pure form.

The phosphopeptides of the present invention or their salts may have utility in the treatment or inhibition of (i) dental diseases such as caries, gingivitis and periodontal disease, (ii) rarefying bone diseases such as osteoporosis and osteomalacia and (iii) diseases relating to malabsorption of minerals.

Accordingly, the present invention provides a composition comprising a peptide or a salt thereof in accordance with this invention and a physiologically acceptable diluent.

The composition may be in the form of a pharmaceutical composition.

The composition may be orally ingestible.

A mixture of phosphopeptides and/or their salts may be used in the composition. In this instance it is preferred that those containing the sequence A-B-C-D-E above predominate.

The phosphopeptide or mixture of phosphopeptides is preferably substantially pure at least to the extent of not containing unpalatable impurities.

Figure 1:
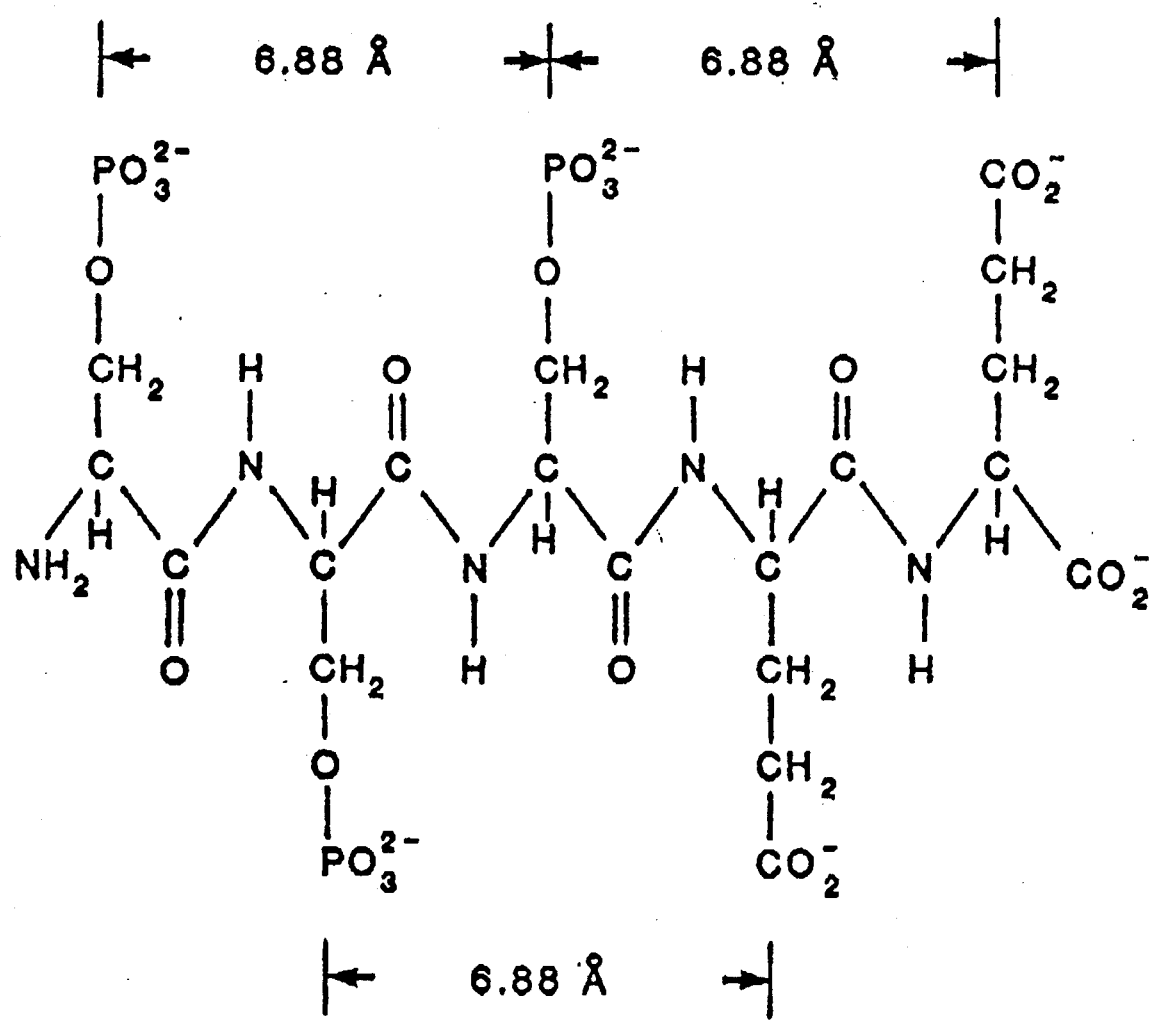
FIG. 1 is a structural formula of a pentapeptide within the scope of the present invention showing spacings of the phosphate and carboxyl groups in a beta-conformation.

The following phosphopeptides have been found to be useful in the compositions of the present invention:

T1. Glu-Met-Glu-Ala-Glu-Pse-Ile-Pse-Pse-Pse-Glu-Glu-Ile-Val-Pro-Asn-Pse-Val-Glu-Gln-Lys,

T2. Glu-Leu-Glu-Glu-Leu-Asn-Val-Pro-Gly-Glu-Ile-Val-Glu-Pse-Leu-Pse-Pse-Pse-Glu-Glu-Ser-Ile-Thr-Arg,

T3. Asn-Thr-Met-Glu-His-Val-Pse-Pse-Pse-Glu-Glu-Ser-Ile-Ile-Pse-Gln-Glu-Thr-Tyr-Lys,

T4. Asn-Ala-Asn-Glu-Glu-Glu-Tyr-Ser-Ile-Gly-Pse-Pse-Pse-Glu-Glu-Pse-Ala-Glu-Val-Ala-Thr-Glu-Glu-Val-Lys, and T5. Glu-Gln-Leu-Pse-Pth-Pse-Glu-Glu-Asn-Ser-Lys.

The amino acid symbols are as follows: Pse-phosphoserine, Ser-Serine, Pth-phosphothreonine, Thr-threonine, Glu-glutamate, Asp-aspartate, Ala-alanine, Asn-asparagine, Gln-glutamine, Gly-glycine, Arg-arginine, His-histidine, Ile-isoleucine, Leu-leucine, Lys-lysine, Met-methionine, Pro-proline, Tyr-tyrosine, Val-valine.

The phosphopeptide may be made synthetically by chemical synthesis or genetic engineering or can be extracted from naturally occurring material.

Because of cost considerations it is currently more economic to extract the phosphopeptide from casein and in particular from alpha-s casein or beta-casein. Phosvitin may also be used as a source of the peptide. Further, phosphoproteins in cereals, nuts and vegetables particularly in bran husks or sheaths may be used to produce the peptide above. In particular, rice, wheat, oat, barley or rye brans. Soybean and meat contain phosphoproteins which may be of use in obtaining the peptide above.

Casein and in particular alpha-s casein or beta-casein or salts thereof such as sodium caseinate contain polypeptides which can be cleaved to simpler peptides. Such cleavage may be effected by digestion, such digestion may be chemical or proteolytic.

It is presently preferred to digest casein with one of trypsin, pepsin, chymotrypsin, papain, thermolysin or pronase. Of these, trypsin is preferred.

The digested casein can be fractioned into peptides including the sequence A-B-C-D-E and other peptides. The presence of said other peptides is not deleterious to efficacy, however, certain of said other peptides have objectionable taste and accordingly if any of said other peptides are to be included it is preferable to remove those having objectionable taste. In general, those of said other peptides having objectionable taste seem to be hydrophobic.

The following peptides have been found to have objectionable taste:

1. Glu-Val-Leu-Asn
2. Asn-Glu-Asn-Leu-Leu
3. Ala-Pro-Phe-Pro-Gln-Val-Phe-Gly
4. Leu-Arg-Phe
5. Phe-Phe-Val-Ala-Pro-Phe-Pro-Gln-Val-Phe-Gly-Lys
6. Leu-Arg-Leu
7. Phe-Tyr-Pro-Glu-Leu-Phe (Glu-glutamate; Val-valine; Leu-leucine; Asn-asparagine; Ala-alanine; Pro-proline; Phe-phenylalanine; Gln-glutamine; Gly-glycine; Arg-Arginine; Lys-lysine; Tyr-tyrosine.)

Preferably the peptide is one exhibiting a reduction in hydroxy apatite dissolution rate of at least 15% under the test conditions defined herein.

Preferably the peptide is one exhibiting a reduction in hydroxy apatite dissolution rate of at least 25% under the test conditions defined herein.

Preferably, the peptide is one exhibiting a reduction in hydroxy apatite dissolution rate of at least 30% under the test conditions defined herein.

Preferably, the peptide is one exhibiting a reduction in hydroxy apatite dissolution rate of at least 32% under the test conditions defined herein.

Preferably, the peptide is present as 0.01 to 10% by weight.

Preferably, the peptide is present as 0.01 to 5% by weight.

Preferably, the peptide is present as 0.01 to 2% by weight.

The composition of this invention may be in the form of a comestible such as foodstuff or confectionery, dentifrice, tablet or comprise a pharmacologically acceptable vehicle or solution of suspension for topical application to the teeth or gingival tissues or a mouthwash. Other modes of administering the peptide would be acceptable if physiologically or pharmacologically acceptable.

Of particular interest as compositions are chewing gum, breakfast foods, ice-cream and other frozen confectionery, confectionery, sweets and cakes as these are all known as caries problem materials. Similar considerations apply to other potentially cariogenic food components.

Also of particular interest are dentifrices, mouthwashes and preparations for topical application to teeth and gingival tissue and enteric capsules for the treatment of bone disorders and mineral malabsorption.

Also of interest is the use of compositions in accordance with this invention in respect of dental treatment of cavities. In this last respect, there appears to be evidence of remineralization of incipient lesions which are considered to be a pre-cavity condition. However, there is also evidence to indicate that application of compositions in accordance with this invention to the surfaces of actual cavities and to surfaces of teeth produced by removal of decay material from actual cavities or by fracture is beneficial.

Since a topical application of a composition in accordance with this invention which is an aqueous solution to surfaces of actual cavities or surfaces of teeth produced by removal of decay material from actual cavities or by fracture is unlikely to have long term effect, we have further sought to provide compositions which might have the desired long term effect.

Accordingly, the present invention also provides a composition in accordance with this invention and adapted to remain in contact with a tooth surface over a prolonged period. The invention also provides methods and means for maintaining compositions in accordance with this invention in contact with a tooth surface over a prolonged period.

In this last respect a prolonged period should be interpreted in accordance with the effect desired and the time taken to achieve sufficient of that effect to be of value. However, in some instances that prolonged period may be as short as one day but is more preferably a period of weeks or months.

In one instance a tooth cavity is coated with a composition in accordance with this invention and the cavity is closed to restrict escape of the composition. Such closure may be effected by capping or use of dental cavity filling compositions.

In another instance the composition is so formulated as to be adapted to remain in place for a prolonged period. In this instance the composition of the invention may form part of a dental filling composition.

Accordingly, the present invention also provides a dental filling composition comprising a phosphopeptide of formula A-B-C-D-E as defined above and a carrier therefor adapted to adhere the composition to a tooth surface.

Such a dental filling composition may contain dental filling materials known per se including amalgams and settable polymers.

Of particular interest are dental filling compositions which contain calcium. The calcium is desirably in the form of calcium phosphate or hydroxyapatite.

The phosphopeptides for use in the invention can be extracted in a number of ways but the use of a fractionation technique is generally preferred.

The phosphopeptides can be extracted by fractionation based on molecular size or charge characteristics. Due to the unique negative charge density and divalent metal ion sequestering ability of the peptides conferred by the active sequence A-B-C-D-E as defined, the preferred fractionation procedure is anion exchange chromatography or selective precipitation or a combination of both.

The following procedure illustrates one mode of extraction.

EXTRACTION PROCEDURE I

An example of the phosphopeptides are those produced by a tryptic digestion of bovine milk casein. The digestion of whole sodium caseinate or fractions (alpha-S or beta) produced by selective precipitation (Zittle, C. A. and Custer J. H.; J. Dairy Sci 46L 1183–1189, 1963) is carried out using a protein:trypsin ratio of 50:1 in 20 mM Tris HCl pH 8.0, 2.5 mM NaCl at 37° C. for 1 h. The peptides were fractionated using a Pharmacia FPLC system with a Mono Q HR 5/5 column and eluted with a NaCl gradient; Buffer A 20 mM Tris HCl pH 8.0, 2.5 mM NaCl; Buffer B 20 mM Tris HCl pH 8.0, 500 mM NaCl, gradient 0–100% Buffer B/30 min; flow rate 1 ml/min. Fractions were washed and concentrated using an Amicon Ultrafiltration Cell with a UMO5 filter. The peptides were identified using a Water Associates PICO-TAG amino acid analysis system using phenylisothiocyanate amino acid derivatisation. Phosphate was measured by the method of Itaya and Ui (Clin, Chim, Acta. 14:361–366, 1960). The peptides were sequenced (after the removal of phosphate by alkaline phosphatase) using manual Edman degradation and the resulting PTH-amino acids identified using reverse phase HPLC on a Zorbax ODS column 25×0.46 cm (DuPont).

The following phosphopeptides were individually obtained from a tryptic digestion of sodium caseinate using the above procedure.

T1. Glu-Met-Glu-Ala-Glu-Pse-Ile-Pse-Pse-Pse-Glu-Glu-Ile-Val-Pro-Asn-Pse-Val-Glu-Gln-Lys.

T2. Glu-Leu-Glu-Glu-Leu-Asn-Val-Pro-Gly-Glu-Ile-Val-Glu-Pse-Leu-Pse-Pse-Pse-Glu-Glu-Ser-Ile-Thr-Arg.

T3. Asn-Thr-Met-Glu-His-Val-Pse-Pse-Pse-Glu-Glu-Ser-Ile-Ile-Pse-Gln-Glu-Thr-Tyr-Lys.

T4. Asn-Ala-Asn-Glu-Glu-Glu-Tyr-Ser-Ile-Gly-Pse-Pse-Pse-Glu-Glu-Pse-Ala-Glu-Val-Ala-Thr-Glu-Glu-Val-Lys.

T5. Glu-Gln-Leu-Pse-Pth-Pse-Glu-Glu-Asn-Ser-Lys.

In addition the following peptides were also obtained:

T6. Asp-Ile-Gly-Pse-Glu-Pse-Thr-Glu-Asp-Gln-Ala-Met-Glu-Asp-Ile-Lys.

T7. Val-Pro-Gln-Leu-Gln-Ile-Val-Pro-Asn-Pse-Ala-Glu-Glu-Arg.

T8. Thr-Val-Asp-Met-Glu-Pse-Thr-Glu-Val-Phe-Thr-Lys.

T9. Leu-Pth-Glu-Glu-Lys.

The peptides T1, T6 and T7 were also obtained from a TPCK-tryptic digest of alpha$_{s1}$-caseinate (comprising alpha$_{s1}$ and alpha$_{s0}$). Peptide T2 was also obtained from a TPCK-tryptic digest of beta-caseinate. Peptides T3, T4, T5, T8 and T9 were also obtained from a TPCK-tryptic digest of alpha$_{s2}$-caseinate (comprising alpha$_{s2}$, alpha$_{s3}$, alpha$_{s4}$ and alpha$_{s6}$). The amino acid symbols are as follows: Pse-phosphoserine, Ser-serine, Pth-phosphothreonine, Thr-threonine, Glu-Glutamate, Asp-aspartate, Ala-alanine, Asn-aspargine, Gln-glutamine, Gly-glycine, Arg-arginine, His-histidine, Ile-isoleucine, Leu-leucine, Lys-lysine, Met-methionine, Pro-proline, Tyr-tyrosine, Val-valine.

EXTRACTION PROCEDURE II

The following procedure illustrates one mode of selective precipitation.

A solution of sodium caseinate was digested with trypsin (50:1, casein:trypsin) for one hour at 37° C. with the pH maintained at 8.0 by the addition of NaOH. HCl (0.1M) was then added to the solution at room temperature to pH 4.7 and the resulting precipitate removed. $BaCl_2$ was added to the supernatant to a level of 0.25% w/v followed by an equal volume of absolute ethanol and the resulting precipitate was removed and dried. The precipitate was dissolved in one tenth the original volume of water (to facilitate dissolution the pH was raised with NaOH) and the solution acidified to pH 3.5 with 1M HCl. An equal volume of acetone was added and the precipitate removed and dried. The precipitate was then redissolved in $H_2O$ and acidified to pH 2.0 by addition of HCl. The resulting precipitate was removed and discarded and the supernatant was adjusted back to pH 3.5 with NaOH and an equal volume of acetone was added. The resulting precipitate was collected, redissolved in water and $H_2SO_4$ added to precipitate $BaSO_4$ which was discarded. The supernatant was then dialysed and lyophylised or spray dried. A mixture of 5 phosphopeptides were obtained with this procedure.

The following are the phosphopeptides obtained:
T1. Glu-Met-Glu-Ala-Glu-Pse-Ile-Pse-Pse-Pse-Glu-Glu-Ile-Val-Pro-Asn-Pse-Val-Glu-Gln-Lys.
T2. Glu-Leu-Glu-Glu-Leu-Asn-Val-Pro-Gly-Glu-Ile-Val-Glu-Pse-Leu-Pse-Pse-Pse-Glu-Glu-Ser-Ile-Thr-Arg.
T3. Asn-Thr-Met-Glu-His-Val-Pse-Pse-Pse-Glu-Glu-Ser-Ile-Ile-Pse-Gln-Glu-Thr-Tyr-Lys.
T4. Asn-Ala-Asn-Glu-Glu-Glu-Tyr-Ser-Ile-Gly-Pse-Pse-Pse-Glu-Glu-Pse-Ala-Glu-Val-Ala-Thr-Glu-Glu-Val-Lys.
T5. Glu-Gln-Leu-Pse-Pth-Pse-Glu-Asn-Ser-Lys.

The ratio of the phosphopeptides (T1:T2:T3:T4:T5) in the final preparation depends on the starting material and conditions of hydrolysis. Digesting sodium caseinate with TPCK-trypsin yields largely T2 with small amounts of T1, T3 and T4. However, T2 shows greater lability than the other peptides such that more rigorous digestion as occurs with some commercial casein digests yields a preparation containing largely T1 with small amounts of T3 and T4.

If in lieu of sodium caseinate, alpha s1-casein is used for this procedure pure T1 is obtained. With beta-casein as the starting material pure T2 is obtained.

The most common sequences of the active peptides is the pentapeptide Pse-Pse-Pse-Glu-Glu. The spacings of the phosphate and carboxyl groups in a beta-conformation of this pentapeptide are shown in FIG. 1.

The 6.88 Angstrom spacings of phosphates and carboxyls allows specific attachment to calcium atoms along the c-axis of hydroxyapatite crystals. This pentapeptide sequence occurs in peptides T1 to T4 and occurs modified in peptide T5 - Pse-Pth-Pse-Glu-Glu following a conservative substitution of phosphothreonine for phosphoserine.

Conservative substitutions within the active sequence would be phosphothreonine and to a lesser extent phosphotryrosine or phosphohistidine for phosphoserine although phosphoserine is preferable. Another possible substitution for phosphoserine would be glutamate or aspartate but again phosphoserine is preferable. A possible substitution for glutamate is aspartate.

The active peptides can sequester calcium phosphate and other salts of divalent metal ions. One mole of T1 binds 16 mole of $CaHPO_4$ such that a 10 mg/ml solution of T1 at pH 7.0 can solubilize 60 mM $CaHPO_4$ producing a metastable supersaturated solution with respect to calcium phosphate species. With chloride as the counter ion one mole of T1 binds only 5 mole of $Ca^{++}$ binding only to serine phosphates. One mole of T1 with about 16 mole of $CaHPO_4$ bound (M.W. 4883) will henceforth be referred to as calcium phosphate T1. An important chemical feature of calcium phosphate T1 is that above 2% w/v in water the composition is a thixotropic gel. T1-T5 have been shown to be potentially anticariogenic using the following test procedures:

TEST 1

Hydroxyapatite Dissolution Rate Assay

This test is a modification of a test procedure already described (Reynolds, E. C., Riley, P. F. and Storey, E. Calcif. Tiss Int 34:s52-s56, 1982). The purpose of this test is to determine the effect of the peptides on hydroxyapetite dissolution and in this respect since tooth enamel is largely composed of hydroxyapatite it is believed that useful comparisons can be made.

Double distilled, deionized water (18 mega ohms/cm) was used throughout. Analytical reagent grade chemicals were obtained from Ajax Chemicals, Australia. Hydroxyapatitespheriodal was purchased from BDH. A chromatography column containing 0.1 g of hydroxyapatite beads was used for the demineralisation assay. Tris 5 mM, pH 8.3 containing 50 mM NaCl was used as the column buffer at 20° C. and was pumped through the column at a rate of 0.1 ml/min. A peptide solution 0.1 mg/ml of buffer was applied to the column and 0.2 ml fractions were collected before and after peptide application and assayed for total calcium, phosphate and peptide. From these values a rate of dissolution (nmol calcium or phosphate per min) for each 0.2 ml fraction was obtained.

Phosphopeptides T1-T5 all decreased hydroxyapatite dissolution rate by about 32%.

Phosphopeptides T6-T9 were found to be much less effective.

Fluoride plus phosphopeptide T1 gave a combined reduction in hydroxyapatite dissolution (40% reduction). The phosphopeptide T1 caused a 50% greater retention of fluoride in the hydroxyapatite column.

This work shows that these phosphopeptides bind to hydroxyapatite and reduce the minerals dissolution rate and enhance the retention of fluoride in the crystal matrix. The reduction in hydroxyapatite dissolution was related to the phosphoserine content and spacings within the peptides.

TEST 2

Intra-Oral Caries Test

The anticariogenicity of phosphopeptide T1 was determined using a modification of the intra-oral caries test of Koulourides and Ostrom (Caries Res. 10:442-482, 1976). Enamel slabs were inset in a removable intra-oral appliance to simulate an approximal area. This was done on both sides of the removable appliance (left and right). The appliance was worn to allow plaque accumulation in the simulated approximal areas. Eight times a day the appliance was removed and placed in a solution at 37° C. The solution was 2% w/v sucrose, 2% w/v glucose, 140 mM KCl, 20 mM NaCl at pH 7.0. Twice a day the right side enamel slabs received exposure to a solution containing 1.8% w/v calcium phosphate T1 in 140 mM KCl, 20 mM NaCl at pH 7.0, while the left side received only the salt solution. At the completion of the experiment the enamel slabs were removed, sectioned and subjected to microradiography and microhardness testing. The microradiography showed that the slabs exposed to the sugar-salt solution (left-side) had sub-surface, caries-like lesions. However, the slabs exposed to the sugar-salt solution and the peptide T1 solution twice a day showed no caries-like changes. The results were confirmed by microhardness analysis. Plaque was also taken from both sides of the appliance and analysed for calcium phosphate, serine phosphate and peptide T1 using a competitive, quantitative, enzyme-linked immunosorbent assay (ELISA) utilising monoclonal antipeptide T1 antibodies.

This showed that the plaque on the right side of the appliance exposed twice a day to the peptide T1 solution contained the peptide at a level of at least 0.4% w/wet wt of plaque and the level of calcium phosphate had increased 2–4 fold.

This work shows that peptide T1 is incorporated into plaque thereby increasing the plaque level of calcium and phosphate so inhibiting the caries process. This method of incorporation and accumulation in dental plaque can be used to carry remineralising and antibacterial ions into plaque and enamel e.g. Ca, $PO_4$, $FPO_3$, Zn, Cu, Sn, Ag, Al, Fe and La.

TEST 3

Intra-Oral Remineralisation

An intra-oral appliance similar to that used in the previous test procedure was used except that the enamel slabs had been previously exposed to a demineralising solution to produce two sub-surface demineralised lesions in each slab. The demineralising solution was a 0.1M lactate buffer pH 5.0 containing 500 mg/L hydroxyapatite and 1% agar. The appliance were worn by subjects for 10 days. Twice each day the appliances were removed and a drop of remineralising solution was placed on the enamel slabs on the right of the appliance. The left-side enamel slabs served as controls. After 10 days the enamel slabs were removed, sectioned and subjected to microradiography. The amount of mineral deposited back into the sub-surface lesions was determined using microdensitometry. The remineralising solution containing 1.8% w/v calcium phosphate T1 pH 7.0 returned 57% of the mineral lost compared with 13% by saliva alone.

TEST 4

Plaque pH Fall

Subjects refrained from oral hygiene for 3–5 days then rinsed with a 5% sucrose solution for 1 min. Plaque samples were removed and pH was measured using the one drop technique. After approximately 5 min the pH fall to around 5.0. However, if the subjects rinsed with a solution containing 1.8% w/v calcium phosphate T1, pH 7.0 15 min before rinsing with the 5% sucrose solution the plaque pH did not fall below 6.7, demonstrating significant pH buffering by the calcium phosphate T1.

While the precise mechanism by which the phosphopeptides exhibit anticariogenic activity is not known, the following speculative theories have been put forward but are not to be taken as binding or limiting.

The phosphopeptides may accumulate in plaque and enamel, buffer plaque acid, prevent enamel demineralisation and enhance remineralisation. The small molecular weight of the phosphopeptides may allow penetration and accumulation in plaque and enamel pores. The phosphopeptides, due to the appropriate spacing of serine phosphate residues, may bind to tooth enamel mineral and prevent demineralisation. The peptides may also carry calcium and phosphate (fluorophosphate on modification) into plaque and enamel, in an appropriate form, possibly allowing spontaneous remineralisation. The phosphoserine residues may also buffer plaque acid. The phosphopeptide may also carry antibacterial metal ions e.g. Zn, Cu, Sn, Ag, Al, Fe and La into plaque and in this way have an antiplaque and antigingivitis effect. The metal ions are carried by the phosphopeptides primarily due to the phosphoserine residues. Phosphopeptides may bind to plaque bacteria and inhibit sugar utilisation.

The ability of these peptides to sequester calcium phosphate can be utilised in the treatment of various rarefying bone diseases. These peptides can significantly increase the absorption of calcium, phosphate and iron in the gut. Hence, pharmaceutical vehicles (e.g. enteric capsules) or foods containing calcium phosphate T1 and ferrous phosphate T1 can be used for the treatment of osteoporosis/osteomalacia and anaemia.

Applicants have formulated various compositions in accordance with this invention as follows. In general, the compositions contain from 0.01–10% by weight of phosphopeptide.

EXAMPLE 1

Flour

In a device for mixing dry substances, 1% by weight of calcium phosphate T1 was blended with flour.

EXAMPLE 2

Cereal

A breakfast cereal was sprayed with a solution of calcium phosphate T1 in water. The cereal flakes were then dried to produce a finished product containing 1% calcium phosphate T1.

EXAMPLE 3

Bread

1% by weight of calcium phosphate T1 was added to the flour during the mixing of ingredients for the manufacture of bread.

EXAMPLE 4

Cake mix

1% by weight of calcium phosphate T1 was added to the dry ingredients in the preparation of a cake mix.

EXAMPLE 5

Confectionery

In the preparation of confectionery 1% by weight of calcium phosphate T1 was added to the final mixture.

EXAMPLE 6

Biscuit

In the preparation of a biscuit/mixture 1% by weight of calcium phosphate T1 was added to the other dry ingredients during mixing.

EXAMPLE 7

Beverage

A beverage was prepared in which 0.1% weight of calcium phosphate T1 had been dissolved.

EXAMPLE 8

Tablet

A tablet was made containing 10% by weight of calcium phosphate T1 together with excipients being flavouring matter and binding material.

In preparation of a typical dentifrice within the scope of this invention, the requisite salt and salts of the selected phosphopeptide are incorporated into dentifrice compositions in any suitable manner depending on whether a powder, paste or liquid preparation is to be produced. For this purpose appropriate preparations of surface-active agents, binders, flavouring materials and other excipients required to achieve the required form of dentifrice are added.

The invention is further illustrated by the following examples:

EXAMPLE 9

Tooth paste

A toothpaste was prepared having the following composition:

| Calcium phosphate T1 | 5.0% by weight |
| --- | --- |
| CMC 7MF | 1.0% by weight |
| Saccharin 450 | 0.2% by weight |
| Glycerin (B.P.) | 25.0% by weight |
| Sodium lauryl sulphate (Empicol 0919) | 5.0% by weight |
| Sodium benzoate | 0.5% by weight |
| Flavour 9/693090 | 0.8% by weight |
| Calcium phosphate | 1.0% by weight |
| Water Deionized | 39.5% by weight |
| Thixosyl 33J | 9.5% by weight |
| Syloid AL-1 | 12.0% by weight |
| Titanium Dioxide 3328 | 0.5% by weight |

EXAMPLE 10

Toothpaste

A preparation as set out in Example 9 was repeated but with the addition of 0.2% sodium fluoride in a suitable form.

EXAMPLE 11

Toothpaste

A preparation as set out in Example 9 was repeated but with the addition of 0.4% stannous fluoride in a suitable form.

EXAMPLE 12

Toothpaste

A preparation as set out in Example 9 was repeated but with the addition of 0.78% monosodium fluorophosphate in a suitable form.

EXAMPLE 13

Toothpowder

The following preparation was made:

| Calcium phosphate T1 | 5.0% by weight |
| --- | --- |
| Soluble saccharin | 0.1% by weight |
| Colour agent | Trace |
| Dibasic calcium phosphate | 94.1% by weight |

EXAMPLE 14

Toothpowder

A preparation as set out in Example 13 was made but with the addition of 0.76% monosodium fluorophosphate in a suitable form.

EXAMPLE 15

Liquid dentifrice

A preparation was made consisting of:

| Sodium alginate | 1.4% by weight |
| --- | --- |
| Calcium phosphate T1 | 2.0% by weight |
| Sodium lauryl sulphate | 1.0% by weight |
| Flavouring | Trace |
| Colouring | Trace |
| Water | 95.5% by weight |

EXAMPLE 16

Liquid dentifrice

As for Example 15 but with 0.5% sodium fluoride added.

EXAMPLE 17

Mouthwash

The following preparation was made:

| Calcium phosphate T1 | 2.0% by weight |
| --- | --- |
| Sodium fluoride | 0.5% by weight |
| Flavouring | Trace |
| Colouring | Trace |
| Water | 97.5% by weight |

EXAMPLE 18

Carbonated beverage 0.1% by weight of calcium phosphopeptide T1 was added to a commercially available carbonated beverage.

EXAMPLE 19

Fruit juice 0.1% by weight of calcium phosphopeptide T1 was added to a commercially available fruit juice.

EXAMPLE 20

Solution for topical application to teeth

| Calcium Phosphate T1 | 2% |
| --- | --- |
| NaF | 0.6 mM |
| ZnAcetate | 0.1 mM |
| $SrCl_2$ | 0.1 mM |

(this solution may be formed into gel by increasing the amount of calcium phosphate T1).

EXAMPLE 21

Dental filling material

| Calcium phosphate T1 | 5% w/w |
| Calcium phosphate | 95% w/w |
| Polymerizer | trace |
| Made as a paste with water | |

The polymeriser used in this example was glutaraldehyde.

EXAMPLE 22

Dental filling material

| Calcium phosphate T1 | 5% w/w |
| Calcium phosphate | 70% |
| Acrylic polymer | 25% |
| Catalyst for polymer | trace |

EXAMPLE 23

Topical Gel for the Treatment of hypersensitive teeth

| Calcium phosphate T1 | 4.0% by weight |
| $SrF_2$ | 1.0% by weight |
| Flavouring | Trace |
| Water | 95% |

In the above calcium phosphate T1 was used for illustration but in lieu any appropriate phosphopeptide and/or salt might be used.

Modifications and adaptations may be made to the above described without departing from the spirit and scope of this invention which includes every novel feature and combination of features disclosed herein. The claims form part of the disclosure of this.

The claims defining the invention are as follows:

1. A composition comprising a phosphopeptide selected from the group consisting of a phosphopeptide comprising the sequence A-B-C-D-E, where A, B, C, D and E are independently phosphoserine, phosphothreonine, phosphotyrosine, phosphohistidine, glutamate and aspartate, a phosphopeptide having the sequence A-B-C-D-E, where A, B and C are independently phosphoserine, phosphothreonine, phosphotyrosine and phosphohistidine and D and E are independently phosphoserine, phosphothreonine, glutamate and asparatate, a phosphopeptide having the sequence A-B-C-D-E where A, B and C are phosphoserine and D and E are glutamate, a phosphopeptide having the sequence Glu-Met-Glu-Ala-Glu-Pse-Ile-Pse-Pse-Pse-Glu-Glu-Ile-Val-Pro-Asn-Pse-Val-Glu-Glu-Lys, a phosphopeptide having the sequence Glu-Leu-Glu-Glu-Leu-Asn-Val-Pro-Gly-Glu-Ile-Val-Glu-Pse-Leu-Pse-Pse-Pse-Glu-Glu-Ser-Ile-Thr-Arg, a phosphopeptide having the sequence Asn-Thr-Met-Glu-His-Val-Pse-Pse-Pse-Glu-Glu-Ser-Ile-Ile-Pse-Gln, Glu-Thr-Tyr-Lys, a phosphopeptide having the sequence Asn-Ala-Asn-Glu-Glu-Glu-Tyr-Ser-Ile-Gly-Pse-Pse-Pse-Glu-Glu-Pse-Ala-Glu-Val-Ala-Thr-Glu-Glu-Val-Lys, a phosphopeptide having the sequence Glu-Gln-Leu-Pse-Pth-Pse-Glu-Glu-Asn-Ser-Lys and salts thereof.

2. A composition as claimed in claim 1 wherein the phosphopeptide is present in a concentration of 0.01% to 10% by weight.

3. A composition as claimed in claim 2 wherein the phosphopeptide is present in a concentration of 0.01% to 5% by weight.

4. A composition as claimed in claim 3 wherein the phosphopeptide is present in a concentration of 0.01% to 2% by weight.

5. A composition as claimed in claim 1 including a pharmaceutically acceptable diluent.

6. A composition as claimed in claim 1 including an orally ingestible diluent.

7. A composition as claimed in claim 6 wherein the orally ingestible diluent is a comestible.

8. A composition as claimed in claim 7, wherein the comestible is a foodstuff or confection.

9. A composition as claimed in claim 1, in the form of a toothpaste, tooth powder, dentifrice, mouthwash or preparation for topical application to teeth or gingival tissue.

10. A composition as claimed in claim 1, in the form of a gel.

11. A composition as claimed in claim 1, in the form of a dental filling composition.

12. A composition as claimed in claim 11 including calcium phosphate or hydroxy apatite.

13. A composition in accordance with claim 1 including a compound selected from the group consisting of calcium phosphate and hydroxy apatite.

14. A composition in accordance with claim 1 including at least one remineralizing or antibacterial ion.

15. A composition in accordance with claim 14 wherein said remineralizing or antibacterial ions is selected from the group consisting of Ca, $PO_4$, $FPO_3$, Zn, Cu, Sn, Ag, Al, Fe and La.

16. A composition in accordance with claim 15 wherein said mineralizing or antibacterial ion is zinc.

17. A composition in accordance with claim 1 wherein said phosphopeptide is a phosphopeptide sodium salt.

18. A phosphopeptide comprising the sequence Glu-Met-Glu-Ala-Glu-Pse-Ile-Pse-Pse-Pse-Glu-Glu-Ile-Val-Pro-Asn-Pse-Val-Glu-Gln-Lys.

19. A salt of a phosphopeptide of any one of claim 18.

20. A salt in accordance with claim 19 wherein said salt is the sodium salt.

21. A phosphopeptide comprising the sequence Glu-Leu-Glu-Glu-Leu-Asn-Val-Pro-Gly-Glu-Ile-Val-Glu-Pse-Leu-Pse-Pse-Pse-Glu-Glu-Ser-Ile-Thr-Arg.

22. A phosphopeptide comprising the sequence Asn-Thr-Met-Glu-His-Val-Pse-Pse-Pse-Glu-Glu-Ser-Ile-Ile-Pse-Gln-Glu-Thr-Tyr-Lys.

23. A phosphopeptide comprising the sequence Asn-Ala-Asn-Glu-Glu-Glu-Tyr-Ser-Ile-Gly-Pse-Pse-Pse-Glu-Glu-Pse-Ala-Glu-Val-Ala-Thr-Glu-Glu-Val-Lys.

24. A phosphopeptide comprising the sequence Glu-Gln-Leu-Pse-Pth-Pse-Glu-Glu-Asn-Ser-Lys.

25. A composition comprising the phosphopeptide of any one of claims 4 to 8 and a physiologically acceptable diluent.

26. A method of obtaining the phosphopeptide of any one of claims 4 to 8 which comprises fractionating a digest of casein, alpha-s-casein, beta casein or a salt thereof.

* * * * *

UNITED STATES PATENT AND TRADEMARK OFFICE
CERTIFICATE OF CORRECTION

PATENT NO.  : 5,015,628                                    Page 1 of 2

DATED       : May 14, 1991

INVENTOR(S) : Eric C. Reynolds

It is certified that error appears in the above-identified patent and that said Letters Patent is hereby corrected as shown below:

add

On the Title Page, after "[22] Filed: Aug. 3, 1990",

--Related U.S. Application Data

[63]   PCT/AU 87/00172 filed June 12, 1987, is a continuation of Ser. No. 191,162, April 12, 1988 Abandoned.

[30]   Foreign Application Data

June 12, 1986 [AU] Australia........PH 6385--

Column 1, line 5: "No. 191,162, filed Apr. 12, 1988, now abandoned.", should read as --No. 191,162, filed as PCT/AU 8700172 on June 12, 1987, now abandoned.--

UNITED STATES PATENT AND TRADEMARK OFFICE
CERTIFICATE OF CORRECTION

PATENT NO. : 5,015,628
DATED : May 14, 1991
INVENTOR(S) : Eric C. Reynolds

It is certified that error appears in the above-indentified patent and that said Letters Patent is hereby corrected as shown below:

Column 11, line 59, Claim 1: "Glu-Glu-Lys" should read as --Glu-Gln-Lys--

Column 11, line 64, Claim 1: "Gln, Glu-Thr-" should read as --Gln-Glu-Thr--

Signed and Sealed this

Twenty-fourth Day of August, 1993

Attest:

BRUCE LEHMAN

Attesting Officer   Commissioner of Patents and Trademarks